(12) United States Patent
Faccioli et al.

(10) Patent No.: US 11,051,945 B2
(45) Date of Patent: Jul. 6, 2021

(54) PROSTHETIC DEVICE WITH ANTIBIOTICS

(71) Applicant: TECRES S.p.A., Sommacampagna (IT)

(72) Inventors: Giovanni Faccioli, Monzambano (IT); Renzo Soffiatti, Nogara (IT)

(73) Assignee: TECRES S.P.A., Sommacampagna (IT)

( * ) Notice: Subject to any disclaimer, the term of this patent is extended or adjusted under 35 U.S.C. 154(b) by 74 days.

(21) Appl. No.: 15/873,254

(22) PCT Filed: Jul. 29, 2016

(86) PCT No.: PCT/IB2016/054548
§ 371 (c)(1),
(2) Date: Jan. 17, 2018

(87) PCT Pub. No.: WO2017/017648
PCT Pub. Date: Feb. 2, 2017

(65) Prior Publication Data
US 2018/0168813 A1 Jun. 21, 2018

(30) Foreign Application Priority Data

Jul. 30, 2015 (IT) .................... 102015000040600

(51) Int. Cl.
| | | |
|---|---|---|
| *A61F 2/36* | (2006.01) | |
| *A61B 17/56* | (2006.01) | |
| *A61F 2/30* | (2006.01) | |
| *A61F 2/38* | (2006.01) | |
| *A61F 2/34* | (2006.01) | |

(52) U.S. Cl.
CPC .................. *A61F 2/30* (2013.01); *A61F 2/34* (2013.01); *A61F 2/36* (2013.01); *A61F 2/3662* (2013.01); *A61F 2/389* (2013.01); *A61F 2002/3068* (2013.01); *A61F 2002/3069* (2013.01); *A61F 2002/30583* (2013.01); *A61F 2002/30593* (2013.01); *A61F 2002/30784* (2013.01)

(58) Field of Classification Search
CPC ................ A61F 9/0017; A61F 9/00781; A61F 2250/0067; A61F 2250/0068; A61F 2002/30677; A61F 2002/30672; A61F 2310/00353; A61F 2002/2817; A61F 2002/2835; A61F 2002/30616; A61F 2002/3068; A61F 2002/30805
See application file for complete search history.

(56) References Cited

U.S. PATENT DOCUMENTS 6,486,232 B1 * 11/2002 Wise .................... A61B 17/866
523/118
2003/0187513 A1 * 10/2003 Durniak ............. A61B 17/8802
623/22.12

(Continued)

FOREIGN PATENT DOCUMENTS

| DE | 10201052914 | 5/2012 |
| WO | 2005/007212 | 1/2005 |

OTHER PUBLICATIONS

International Search Report dated Nov. 10, 2016 for PCT/IB2015/054548 (3 pages).

*Primary Examiner* — Ann Schillinger
(74) *Attorney, Agent, or Firm* — Tutunjian & Bitetto, P.C.

(57) ABSTRACT

Prosthetic device suitable for being implanted in a bone or joint site of the human body, including a prosthetic body, wherein the prosthetic device includes or can be added with antibiotic or a medical substance.

15 Claims, 4 Drawing Sheets

(56) References Cited

U.S. PATENT DOCUMENTS

| | | | |
|---|---|---|---|
| 2010/0042214 A1* | 2/2010 | Nebosky | A61B 17/56 623/16.11 |
| 2011/0218644 A1* | 9/2011 | Meridew | A61F 2/3662 623/23.15 |
| 2015/0051539 A1 | 2/2015 | Lin | |
| 2015/0250598 A1 | 9/2015 | Yakimicki et al. | |

* cited by examiner

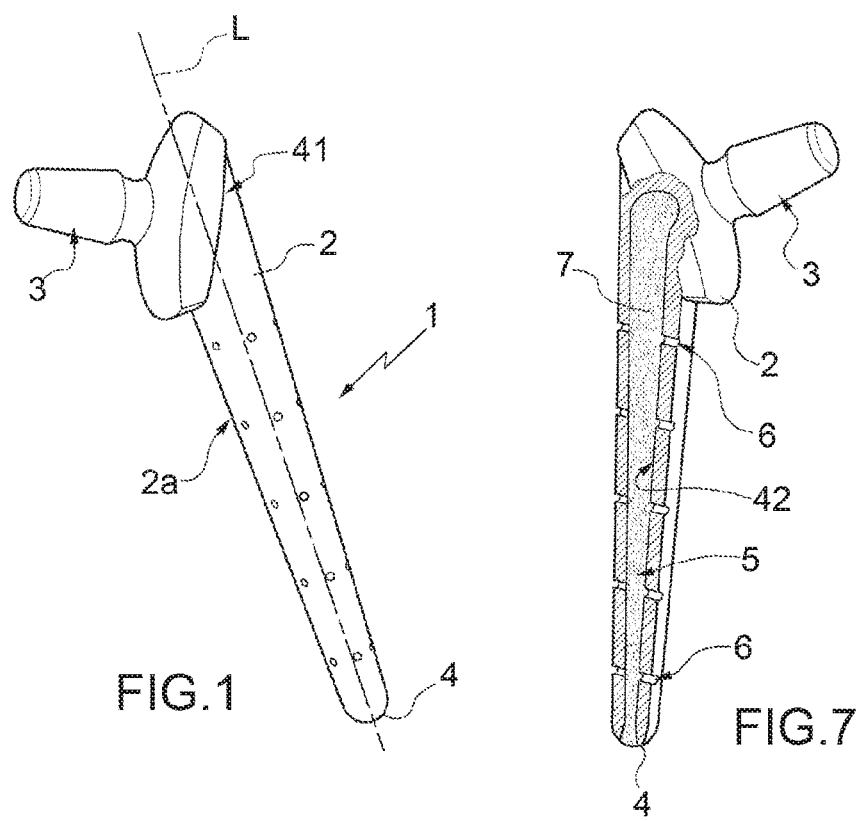
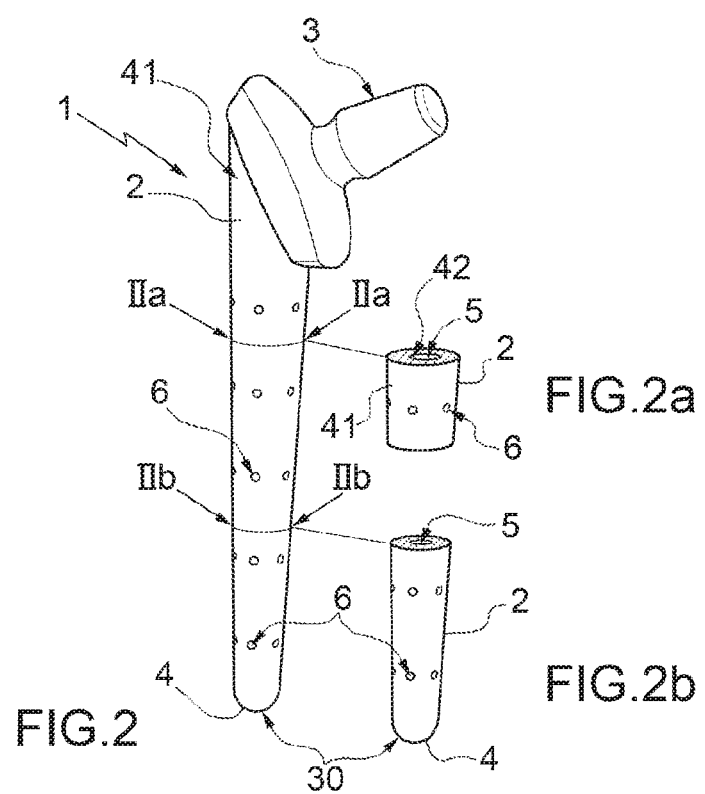

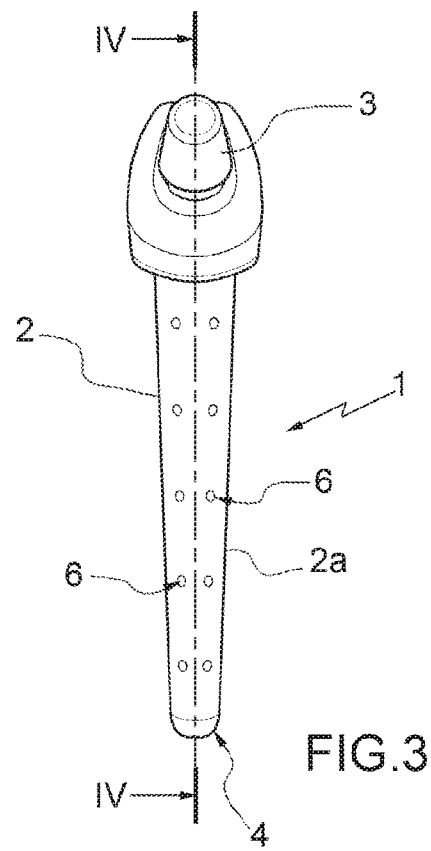
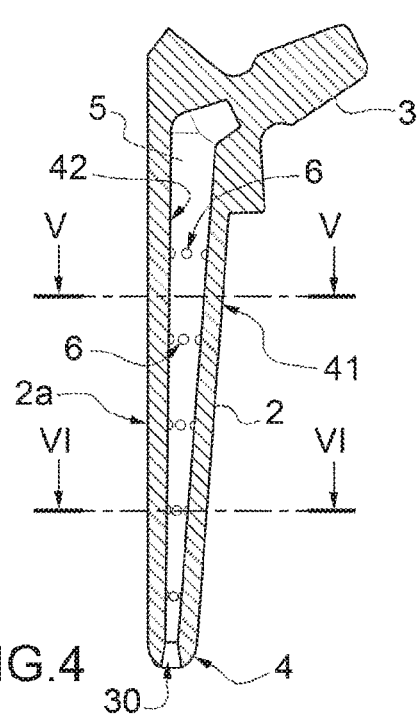
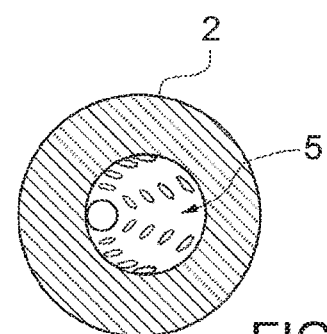
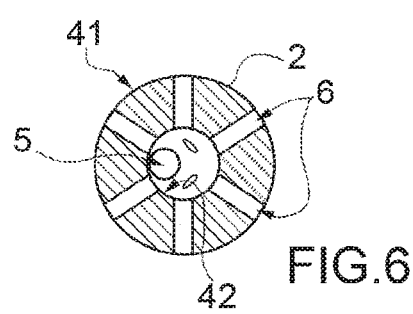
FIG.3
FIG.4
FIG.5
FIG.6

PROSTHETIC DEVICE WITH ANTIBIOTICS

TECHNICAL FIELD OF THE INVENTION

The present invention regards a prosthetic device suitable for being implanted at a bone or a joint of the human body, wherein said prosthetic device is an antibiotic-loaded prosthetic device.

In particular, such prosthetic device is capable of eluting or diffusing an antibiotic substance in order to prevent the onset of an infection or cure an infection underway.

DESCRIPTION OF RELATED ART

It is known that the prostheses implanted within the human body can be subjected to infections.

If this should occur, the infected prosthesis must in fact be removed from the implant site and, before the implant of a new prosthesis, it is necessary to eradicate the infection. During such step, spacer devices are normally employed in order to maintain substantially unchanged the shape of the bone site or of the joint site in which the new prosthesis will be implanted, simultaneously releasing substances capable of treating the infection.

Such procedure is known as "two-stage treatment" for the removal of an infected prosthesis and the implant of a new prosthesis.

Nevertheless, sometimes, when the bone conditions allow, the surgeon decides to not carry out such procedure in two stages, but rather to apply a one stage treatment according to which, after having removed the infected prosthesis and carried out the "cleaning" of the surgical site, the new prosthesis is immediately inserted into the surgical site, without having first used a spacer device for treating the infection.

In such case, the new prosthesis can be fixed to the bone of the patient with bone cement, e.g. antibiotic bone cement, or it can also only inserted in the bone, in accordance with the specific situations. When the prosthesis is inserted in the bone without the use of bone cement, it is more easily removable in case of onset of a new infection. Naturally, if the bone conditions are quite compromised, the use of the bone cement for fixing the new prosthesis is substantially required.

Surgeons who decide to use the "one stage" therapy trust in the fact that the cleaning or renewal of the bone and the systemic antibiotic therapy are sufficient for treating the infection underway or for preventing the onset of a new infection. Nevertheless, from studies carried out, it is seen that in this case the reinfection can occur even if in a small percentage, which is different from what occurs with the two stage treatment where the onset of a new infection is an extremely rare occurrence.

Gels or similar substances are available on the market that are capable of being applied, for example swabbed, on the outer surface of a prosthesis before the implant thereof. Such procedure can be applied both on a first insertion prostheses and on revision prostheses, i.e. implanted following the explant of a first insertion prosthesis.

Such gels or substances, while being antibiotic-loaded, are nevertheless ineffective against bacteria since the contact time with the bacteria themselves is overly reduced, in order to cause the death thereof. Usually, in fact, such substances are used to prevent bacteria, e.g. bacteria present in the outside environment, from being present or settling on the outer surface of the prosthesis, thus preventing the same from entering into the surgical site, even if they are not specifically able to eliminate the bacteria present within the bone or joint site of the implant.

There is therefore the need for the surgeon to be able to implant prosthetic devices, both first implant and revision prosthetic devices, capable of preventing the onset of infections or capable of curing those present.

SUMMARY OF THE INVENTION

The task of the present invention is to improve the state of the prior art.

In the scope of such technical task, one object of the present invention is to provide a prosthetic device capable of preventing the onset of infections or capable of treating those present in the surgical site in which the prosthetic device itself is implanted.

Another object of the present invention is to provide a prosthetic device that is both of first implant and revision.

A further object of the present invention is to provide a prosthetic device with mechanical properties comparable to those of the conventional final prostheses.

In accordance with one aspect of the present invention, prosthetic device is provided according to the present specification.

In accordance with another aspect of the present invention, a kit is provided comprising a prosthetic device according to the present specification.

In accordance with a further aspect of the present invention a method is provided for obtaining a prosthetic device according to the present specification.

The present specification refers to preferred and advantageous embodiments of the invention.

BRIEF DESCRIPTION OF THE DRAWINGS

Further characteristics and advantages of the present invention will be clearer from the detailed description of a preferred but not exclusive embodiment of a prosthetic device, illustrated as a non-limiting example in the enclosed drawing tables, in which:

FIG. 1 is a partially rear perspective view of a portion or of a version of the prosthetic device according to the present invention;

FIG. 2 is a partially front perspective view of a portion or a version of the prosthetic device according to the present invention;

FIG. 2a is a perspective view of a detail sectioned along the transverse trace plane IIa-IIa of FIG. 2;

FIG. 2b is a perspective view of a detail sectioned along the transverse trace plane IIb-IIb of FIG. 2;

FIG. 3 is a front portion of the portion or of the version of the prosthetic device of FIG. 2;

FIG. 4 is a longitudinal section view along the trace plane IV-IV of FIG. 3;

FIG. 5 is a cross section view along the trace plane V-V of FIG. 4;

FIG. 6 is a cross section view along the trace plane VI-VI of FIG. 4;

FIG. 7 is a longitudinal section view of the portion or of the version of the prosthetic device of FIG. 1 or 2, in which the fill material thereof is visible;

FIG. 10b is a side section view of an acetabular portion or version of the prosthetic device of FIG. 10a.

DETAILED DESCRIPTION OF THE INVENTION

Figure 8:
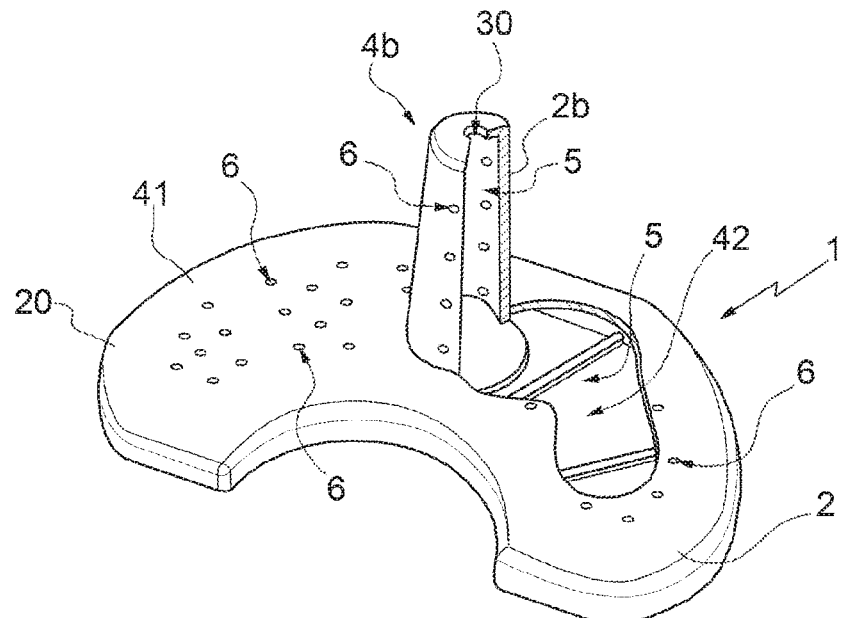
FIG. 8 is a partially transparent perspective view of a tibial portion or version of the prosthetic device according to the present invention.

With reference to the enclosed figures, a prosthetic device according to the present invention is overall indicated with reference number 1.

Such prosthetic device 1 comprises a permanent prosthesis, whether it is a first implant prosthesis or a so-called revision prosthesis, i.e. inserted following the implant of a spacer device in a two stage treatment procedure.

Such prosthetic device 1 can be a hip prosthesis (such as the portions illustrated in FIGS. 1 to 7, 10a, 10b and 11), a shoulder prosthesis, an elbow prosthesis, a knee prosthesis (such as the tibial portions illustrated in FIGS. 8 and 9) or a bone prosthesis in general.

The prosthetic device 1 comprises a prosthetic body 2.

The prosthetic device 1 or the prosthetic body 2 comprises or can be added with antibiotic or a medical substance, as will be better described hereinbelow in the present description.

The prosthetic body 2 comprises, in one version of the invention, at least one tubular wall, said tubular wall having an outer surface 41 as well as an inner surface 42 delimiting the inner cavity 5. In FIGS. 1 to 7, as prosthetic body, a stem component 2a of a hip prosthesis is depicted, as a non-limiting example of the prosthetic device 1 according to the present invention. Generally, the prosthetic body 2 comprises a wall which has an outer surface 41 and an inner surface 42 delimiting the inner cavity 5.

When the prosthetic device according to the present invention comprises a hip prosthesis, it can include a head component intended to be implanted in the acetabular cup of a patient and a stem component 2a, delimited by the tubular wall of the prosthetic body 2 and intended to be implanted in the femur of a patient.

The stem component 2a projects upward from the head component and has elongated shape with a first base end proximal to the head component as well as a second tip end 4; the inner cavity 5 is delimited within the stem component 2a so as to have a substantially elongated extension around the longitudinal extension axis L of the stem component 2a, from its first end to its second end 4.

In one version of the invention, the stem component 2a has a substantially longitudinal progression, along the longitudinal extension axis L, and has a tapered shape starting from the first base end up to the second tip end 4. At the first base end, a neck portion 3 is present adapted to come into contact with the head component.

The neck portion 3 is placed at the hip joint of the human body. The second tip end 4, instead, is adapted to be inserted within the medullary canal of the femoral bone of the patient. The stem component 2a or the prosthetic device 1 or the prosthetic body 2 has, as stated above, an inner cavity 5.

The inner cavity 5, in this version of the invention, has a shape substantially corresponding to that of the prosthetic device 1 or of the prosthetic body 2 at whose interior it is obtained.

According to the embodiment represented in the figures, the inner cavity 5 of the stem component 2a has a substantially longitudinal shape along the longitudinal axis L.

The inner cavity 5 of the stem component 2a has a substantially continuous shape, from the neck portion 3 to the second tip end 4 of the component 2a.

The size of the inner cavity 5 is reduced with respect to the overall size of the prosthetic device 1, so as to not reduce or affect the mechanical properties of the prosthetic device 1 according to the present invention.

Indeed, the prosthetic device can be positioned during use within a bone or joint site and it must be able to support the weight of the user and/or the movements tied to the area in which it is implanted.

With respect to a completely solid prosthetic device, e.g. a prosthesis of conventional type, therefore, the presence of the inner cavity 5 must not compromise the mechanical properties of the prosthetic device itself.

The prosthetic device 1 according to the present invention further comprises holes or ports 6.

Such holes or ports 6 are, according to one version of the invention, evenly distributed along the entire wall and/or the outer surface 41 of the prosthetic device 1.

In the enclosed figures, only some holes or ports 6 are present, without at all limiting the number or arrangement thereof.

The holes or ports 6 are formed transversely to the wall of the prosthetic body 2, so as to be extended from the inner surface 42 to the outer surface 41 thereof.

According to one version of the invention, the prosthetic device 1 has a plurality of holes or ports 6.

Such ports or holes 6 are adapted to place in communication the space corresponding to the inner cavity 5 with the space outside the prosthetic device 1 or with the bone tissue surrounding the prosthetic device 1 during use.

In particular, such holes or ports 6 pass through the inner cavity 5 and the space outside the prosthetic device 1 and hence pass through the wall of the prosthetic device 1 or pass from the outer surface 41 to the inner surface 42 thereof.

The size of the holes or ports 6 are such to allow the passage, in both senses, of liquids or gases, e.g. biological liquids, medicated substances, etcetera.

The inner cavity 5, according to one version of the invention, is adapted to comprise, contain or house a filler material 7.

Therefore, in one version of the invention, the prosthetic device 1 comprises a filler material 7, housed in the inner cavity 5.

The filler material 7 is in fluid, solid or solidifiable fluid form.

In one version of the invention, the filler material 7, when arranged inside the inner cavity 5, is hardened. The filler material 7 is arranged at the entire extension of the inner cavity 5 and, possibly, of the holes or ports 6 so as to constitute a zone 7a for the absorption and subsequent elution of an antibiotic or medical substance or a solution comprising an antibiotic or medical substance.

In addition, in such a manner, the filler material 7 at least partially assists to re-establish the mechanical properties of a prosthetic device according to the invention, in a manner similar to that of a solid prosthesis of conventional type.

In particular, when the filler material 7 is arranged or penetrates into the holes or ports 6, the continuity of the outer surface of the prosthetic body 2 is re-established.

In one version of the invention, the prosthetic device 1 comprises at least one solution comprising an antibiotic or medical substance, such solution being absorbed by the filler material 7.

In one version of the invention, the filler material 7 comprises at least one from among the following materials: acrylic resin, composite material comprising calcium phosphate or an inorganic salt, calcium sulphate, bioglass, polyvinyl alcohol, a mixture thereof. In a further version of the invention, the filler material 7 comprises an absorbent material, such as for example a thread of silk or cotton, or a biocompatible plant fiber or a woven or non-woven fabric, capable of absorbing and being soaked with a medical solution, e.g. antibiotic.

In a still further version of the invention, the filler material 7 comprises a biocompatible semi-solid material comprising a medical substance, such as an antibiotic. Such semisolid material can be insoluble (for example bone cement) or soluble, e.g. animal collagen, sugars, cellulose, etcetera.

The main characteristic of such filler material 7 is that of having capillary capacity, i.e. of comprising, substantially for the entire volume thereof, small channels with micrometric transverse size (i.e. considering the dimension perpendicular to that of greater extension of the small channel itself), capable of absorbing and eluting liquids via capillarity.

Such small channels can be interconnected and they are preferably interconnected in one version of the invention.

In one version of the invention, the filler material 7 comprises an acrylic resin and an inorganic salt, such as PMMA (polymethylmethacrylate) and calcium phosphate or tri-calcium phosphate (TCP).

In one version of the invention, the average cross-section diameter of such small channels is less than 100 microns.

Figure 9:
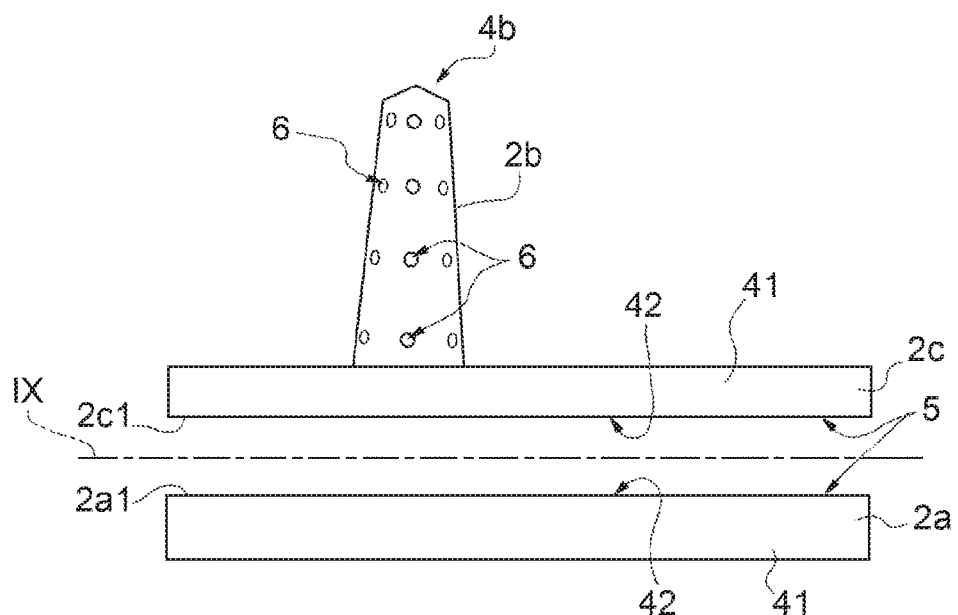
FIG. 9 is a side view of a diagram relative to the tibial portion or version of the prosthetic device of FIG. 8.

In FIGS. 8 and 9, one version of the present invention is illustrated, in which the prosthetic device 1 or the prosthetic body 2 comprises a tibial portion of a knee prosthesis. Such version has the same characteristics as that just described above, it only varies with regard to the shape, which is specific for the implant site in which it must be positioned.

The prosthetic body 2 comprises at least one wall, said wall having an outer surface 41 as well as an inner surface 42 delimiting the inner cavity 5. As prosthetic body, a stem component 2b and a tibial plate component 20 of the tibial portion of a knee prosthesis are depicted, as non-limiting example of the prosthetic device 1 according to the present invention.

The stem 2b has a substantially tubular wall while the tibial plate component 20 has a substantially box-like wall.

The prosthetic body 2, in particular the tibial plate component 20, in one version of the invention illustrated as an example in FIG. 9, is composed of at least two parts: a first portion or shell 2a and a second portion or shell 2c.

Such first portion or shell 2a and second portion or shell 2c comprise the aforesaid wall which has an outer surface 41, an inner surface 42 and delimits the inner cavity 5. In particular, in one version of the invention, the first portion or shell 2a comprises a semi-wall and a semi-cavity 5 of the prosthetic body 2, and analogously the second portion or shell 2c comprises a semi-wall and a semi-cavity 5 of the prosthetic body 2; at least the first portion or shell 2a or at least the second portion or shell 2c or both are hollow portions. Their cavity constitutes the inner cavity 5 of the prosthetic body 2.

Therefore, each of such first portion or shell 2a and second portion or shell 2c form a part of the prosthetic body 2 and, once joined together, they constitute the entire prosthetic body 2 and the entire cavity 5 comprised therein.

As illustrated in FIG. 9, the second portion or shell 2c also comprises the stem component 2b.

The first portion or shell 2a is joined with the second portion or shell 2c by means of a respective peripheral edge 2a1 and 2c1 thereof. In FIG. 9, such peripheral edges 2a1 and 2c1 lie along a transverse plane IX-IX.

The stem 2b is adapted to be inserted in the tibial medullary canal, at the knee joint. Such prosthetic device could also comprise a femoral portion of a knee prosthesis, not illustrated but configured in a conventional manner, or preferably having the same characteristics of the tibial portion described herein.

In one version of the invention, also the femoral portion could be composed of a first portion or shell (e.g. condylar) and a second portion or shell (e.g. of rotation), which, being hollow, delimit an inner cavity.

Also such portions can be joined by means of respective outer peripheral edges, made in their lateral wall, so as to constitute, once joined, the inner femoral portion of the prosthetic device according to the present invention.

The stem component 2b protrudes from the tibial plate component 20, in particular from the lower surface thereof, and has elongated shape with a first base end proximal to the tibial plate component 20 as well as a second tip end 4b, so as to have an extension substantially elongated around the longitudinal extension axis of the stem component 2b, from its first end to its second end 4b.

The inner cavity 5 is delimited within the stem component 2b and within the tibial plate component 20, in order to carry out an improved function. In one version of the invention, the cavity 5 can be delimited only with one of said elements.

The stem component 2b or the tibial plate component 20 or the prosthetic device 1 or the prosthetic body 2 has, as stated above, an inner cavity 5.

The inner cavity 5 has, in this version, a shape substantially corresponding to that of the prosthetic device 1 or of the prosthetic body 2 at whose interior it is obtained.

The inner cavity 5 of the stem component 2b and of the tibial plate component 20 has, in one version of the invention, a substantially continuous shape.

Also in this version, the prosthetic device 1 according to the present invention further comprises holes or ports 6, with configuration and arrangement analogous to the previously described embodiment.

In addition, the inner cavity 5 is adapted to contain or house a filler material 7, which has the characteristics indicated in the present description.

The prosthetic device 1 or the prosthetic body 2 can be made of a biologically compatible material, of the type implantable inside the human body, such as metal, e.g. steel or titanium, metal alloys, plastic or acrylic resins, polymer materials, etcetera. The material of the prosthetic device 1, in any case, must be able to ensure the necessary mechanical properties, for example for support of the weights and/or for wear resistance, adapted to perform the function of permanent bone prosthesis.

The prosthetic device or the prosthetic body 2 is massive, and in one version of the invention it does not have planes of junction between its components, for example the stem 2a and the neck portion 3 or between the tibial plate component 20 and the stem 2b, and is hollow.

In one version of the invention, also the prosthetic body 2 of the device relative to a femoral hip prosthesis can comprise a first portion or shell and a second portion or shell. Such portions, being hollow, delimit the cavity 5 at their interior, and once joined together they constitute the entire prosthetic body 2. In such version of the invention, the first portion or shell and the second portion or shell mirror each other.

The filler material 7 comprises, in one version of the invention, an antibiotic or medical substance.

For example, the antibiotic is adapted to oppose an infection underway in the implant zone of the prosthetic device 1 or to prevent the onset of an infection.

In a further version of the invention, the filler material 7 is adapted to absorb, due to the capillarity given by its small channels, a solution containing an antibiotic or medical substance or an antibiotic or medical substance.

In addition, the presence of the small channels of the filler material 7 and of the holes or ports 6 of the prosthetic device 1 allows the antibiotic or medical substance or the solution comprising the same, contained in the filler material 7, to be eluted or delivered outside the prosthetic device 1, i.e. towards the bone tissue or towards the joint space of the implant site. The antibiotic substance or medical substance exits from the prosthetic device 1 by means of the holes or ports 6.

If the filler material 7 also comprises calcium or other inorganic salts, together with the delivery of the antibiotic or the medical substance, also such calcium or such salts or ions thereof can be eluted or delivered.

Such inorganic substances are beneficial for the surrounding bone tissue with which they come into contact.

The filler material 7 (and at least partially, in some versions, the material of the prosthetic device 1) absorbs the antibiotic or medical substance. Therefore, in one version of the invention, the filler material 7 is absorbent.

According to a further version of the invention, the filler material 7 is porous.

The inner cavity 5, and the filler material 7, therefore act as a tank for the antibiotic or medical substance or for the solution containing the same, which is then released by the spacer device 1 through the holes or ports 6.

In the exemplifying version illustrated in FIGS. 1-7, the stem component 2a is made of a single piece with the neck portion 3. This aspect is tied to the need, for the prosthetic device 1, to sustain the stresses due to the support of the user's weight. Specifically, in fact, the neck portion 3 is the maximum stress zone, in the case of a hip prosthesis.

As stated above, a hip prosthesis of conventional type comprises a hemispherical head adapted to articulate with the acetabular cup or the acetabulum of the hip.

Also such hemispherical head, not illustrated in the figures, can be made according to the present invention, i.e. comprising an inner cavity, this time with shape corresponding to that of the head, and hence at least partially hemispherical, adapted to contain the filler material and thus the antibiotic or medical substance.

In order to allow the exit of the antibiotic or medical substance or of the solution containing the same, the head comprises holes or ports with size such to not interfere with the rotation movement and/or partial translation of the head itself in its joint implant zone. Such prosthetic device 1, due to its particular structure and to the filler material 7 contained therein, allows having a greater exposure, in terms of time and/or of concentrations, to antibiotic or medical substance. Therefore, unlike what occurs for the prostheses of the prior art, it is possible to cure an infection underway in the bone tissue relative to the implant site, or to prevent the onset of a new infection.

Indeed, the delivery/elution of the antibiotic or medical substance lasts for at least one day.

Figure 10A:
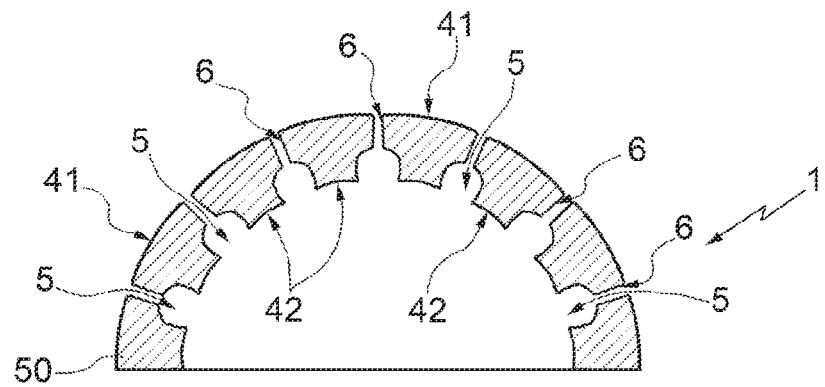
FIG. 10a is a side section view of an acetabular portion or version of the prosthetic device according to the present invention.
Figure 10B:
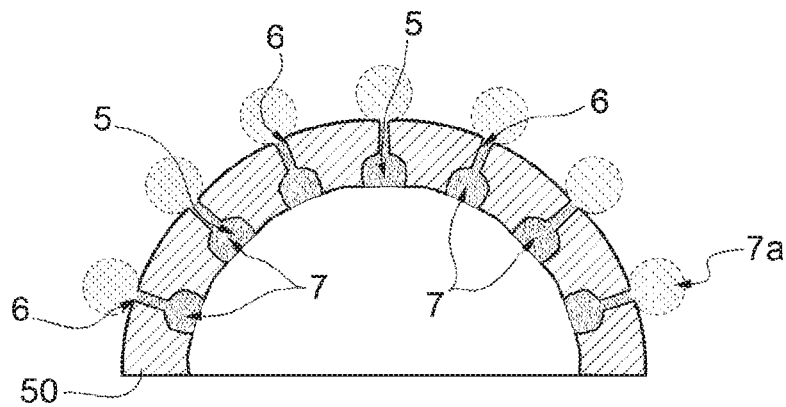
Figure 11:
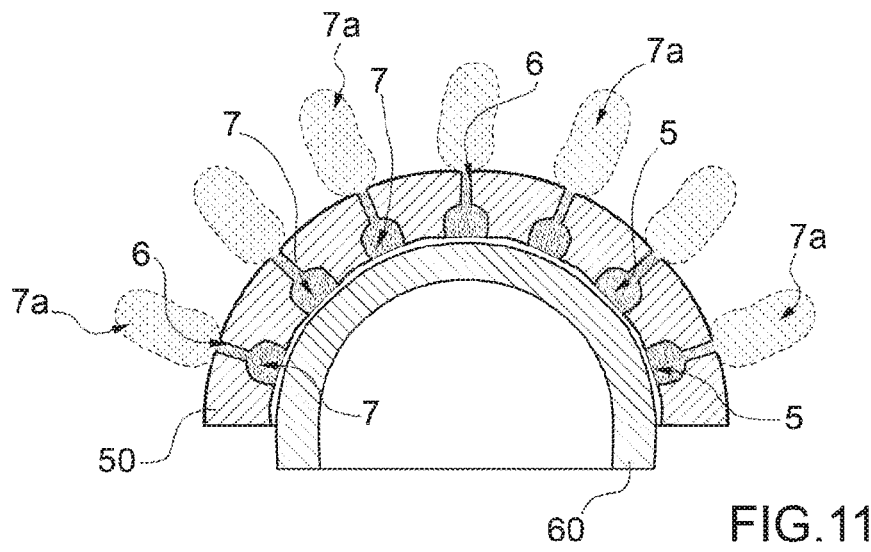
FIG. 11 is a side section view of a further version of the acetabular portion or version of the prosthetic device of FIG. 10b.

In FIGS. 10a, 10b and 11, an acetabular version of the present invention is illustrated, in which the prosthetic device 1 or the prosthetic body 2 comprises an acetabular cup 50 or acetabular portion of a hip prosthesis.

The acetabular cup 50 has dome or hemispherical shape; it constitutes the upper part of a total hip prosthesis.

The acetabular cup 50, during use, is inserted and/or fixed in the acetabular cavity or cup, at the pelvis of the patient.

Such version has the same characteristics as that just described above, but it varies with regard to shape, which is specific for the implant site where it must be positioned.

The prosthetic body 2 comprises at least one wall, said wall having an outer surface 41 as well as an inner surface 42 delimiting the inner cavity 5.

In particular, the outer surface 41 of the acetabular cup 50 is convex and adapted to come into contact with the bone of the patient; the inner surface 42 is concave, and adapted to be joined, possibly by means of interposition of a joint insert 60, with the head of the hip prosthesis connected to the femoral component thereof.

The inner surface 42 delimits a joint cavity with hemispherical shape, substantially complementary to that of the prosthetic head of the hip prosthesis.

The thickness of the wall of the acetabular cup 50, delimited between the outer surface 41 and the inner surface 42, houses the holes or ports 6 and a plurality of cavities 5.

In particular, the holes or ports 6 have a configuration and arrangement analogous to the previously described.

The cavities 5 have, in this version, a shape substantially hemispherical or in any case they correspond with a space at whose interior it is possible to house the filler material 7.

In particular, a cavity 5 is present at one hole or port 6, or a cavity 5 is present at some holes or ports 6 close to each other.

In a further version of the invention, the inner cavity 5 has a substantially continuous shape, corresponding to the inner surface 42 of the acetabular cup 50.

As stated above, the at least one inner cavity 5 is adapted to contain or house a filler material 7, which has the characteristics indicated in the present description.

Outside of the acetabular cup 50, at the bone tissue and at the outside opening of the holes or ports 6, a zone 7a is delimited for the absorption and subsequent elution of an antibiotic or medical substance or a solution comprising an antibiotic or medical substance, possibly contained in the filler material 7.

At the inner surface 42 of the acetabular cup 50, a joint insert 60 can be present. The joint insert 60 is an insert made of ceramic or polyethylene which articulates with the head of the hip prosthesis. Indeed, such joint insert 60 ensures a smooth sliding surface with limited friction, in order to facilitate the sliding of the prosthetic head and hence the movements of the hip joint of the patient.

When present, the joint insert 60, inserted in contact with the inner surface 42 of the acetabular cup 50, closes the at least one cavity 5 from the inner side in a manner such that the zone 7a for the absorption and subsequent elution of an antibiotic or medical substance or a solution comprising an antibiotic or medical substance is only directed towards the outside of the acetabular cup 50.

The present invention further refers to a kit comprising the above described prosthetic device 1 and the filler material 7.

Finally, the present invention refers to a method for obtaining a prosthetic device 1 according to the present invention, comprising the steps of arranging a prosthetic device 1, suitable for being implanted in a bone or joint site of the human body, and arranging a filler material 7.

Such step for arranging the prosthetic device 1 comprises, in one version of the invention, arranging a first portion or shell of the prosthetic body 2 and a second portion or shell of the prosthetic body 2. Such first and second portion or shell delimit the inner cavity 5 of the prosthetic device 1 or each delimits a semi-cavity.

In such version, the first portion or shell is joined with the second portion or shell in a manner so as to obtain a single prosthetic body 2 that is internally hollow.

The joining of the first portion or shell to the second portion or shell can occur via welding or melting or softening of the materials that constitute the prosthetic body 2.

The method then provides for inserting, for example by means of injection or positioning, the filler material 7 in the inner cavity 5 of the prosthetic device 1.

The filler material 7 can be inserted or positioned in the prosthetic device 1 through an opening 30 or multiple openings 30 suitably arranged therein.

In the version in which the prosthetic device 1 is a hip prosthesis, such opening 30 is provided at the second tip end 4 of the stem component 2a.

When instead the prosthetic device is a tibial portion of a knee prosthesis, such opening 30 is provided in the end of the stem 2b, adapted to penetrate into the tibial medullary canal. Possibly, the filler material 7 is allowed to harden, once inserted or positioned in the aforesaid inner cavity 5.

Once the filler material 7 is inserted or positioned, the surgeon can immerse the prosthetic device 1 within a solution comprising an antibiotic or medical substance, in a manner such that the same can penetrate by means of the holes or ports 6 within the prosthetic device and then, via capillarity, within the filler material 7.

In one version of the invention, the filler material 7 is soaked with the aforesaid solution.

In such a manner, once the prosthetic device 1 is implanted in the human body, the solution containing an antibiotic or medical substance will be released by the filler material 7 and can exit, always through the holes or ports 6, towards the surrounding bone tissue, where it will carry out its antibiotic or antimicrobial function.

An advantage conferred by the present invention is the fact that the antibiotic or medical substance is substantially delivered by the entire surface of the prosthetic device in contact with the bone tissue or is in any case capable of reaching all the bone tissue in contact with the prosthetic device according to the present invention.

Studies conducted in the field have in fact revealed that the bone tissue absorbs, in a concentrated manner, all the antibiotic molecules (even only a few) that come into contact therewith. In such case, the quantity of antibiotic or medical substance locally reaches the effective concentration for eradicating the infection.

For this reason, it is essential that the holes or ports 6 are substantially present over the entire outer surface of the prosthetic device 1, in a manner such to be extended over the entire area of contact with the bone tissue and thus, if present, of the infection.

The given definition of "porous" element, present in the present description, can be substituted with "semi-permeable", without departing from the protective scope of the present invention.

The invention thus conceived is susceptible of numerous modifications and variants, all falling within the scope of the inventive concept.

The characteristics presented for one version or embodiment can be combined with the characteristics of another version or embodiment, without departing from the protective scope of the present invention.

In addition, all details can be substituted with other technically equivalent elements. In practice, the materials used, as well as the contingent shapes and sizes, can be of any type in accordance with the requirements, without departing from the protective scope of the following claims.

The invention claimed is:

1. A prosthetic device suitable for being implanted in a bone or joint site of the human body, comprising:
    a prosthetic body, wherein said prosthetic device comprises at least one inner cavity, and through holes or ports extending from said at least one inner cavity to an outer surface of said device and intended to put said at least one inner cavity in communication with the outer surface of the prosthetic device or with the bone tissue surrounding, in use, said prosthetic device,
    wherein the prosthetic body comprises a stem component having a wall having an outer surface as well as an inner surface delimiting said at least one inner cavity,
    said stem component having an elongated shape with a first base end proximal to a neck portion, and a second tip end, said at least one inner cavity being delimited within said stem component so as to present a substantially elongated development around an axis of longitudinal extension (L) of said stem component from said first base end to said second tip end,
    wherein said through holes or ports are evenly distributed along an entire outer surface of the stem component from the first base end to the second tip end,
    wherein said prosthetic device comprises at least one filler material comprising a solidifiable fluid arranged and hardened inside at least one of said at least one inner cavity and said holes or ports so as to constitute a zone for the absorption and subsequent elution of an antibiotic or of a solution comprising said antibiotic,
    wherein said filler material has small interconnected channels which have an average cross-section diameter lower than 100 microns.

2. The prosthetic device according to claim 1, wherein said at least one inner cavity has a shape substantially corresponding to a shape of the prosthetic body or a hemispherical shape or delimits a space suitable for accommodating the filler material.

3. The prosthetic device according to claim 1, wherein said prosthetic body is made of a biologically compatible material implantable in the human body.

4. The prosthetic device according to claim 1, comprising at least one opening for access to said at least one inner cavity to insert the filler material in the at least one inner cavity.

5. The device according to claim 4, wherein said opening is provided at said second tip end.

6. The prosthetic device according to claim 1, wherein said holes or ports are arranged transversely to said wall so as to extend from said inner surface to said outer surface.

7. The prosthetic device according to claim 6, comprising a tibial portion of a knee prosthesis and including a tibial plate component and a stem, wherein said stem is intended to be implanted in the medullary canal of a patient, wherein said tibial plate component and said stem are delimited by said wall, said stem component protruding from said tibial plate component, said stem component having an elongated shape with a first base end proximal to said tibial plate component and a second tip end, said inner cavity being delimited by said stem component and/or within said tibial plate component so as to have a development substantially corresponding to that of said prosthetic device.

8. The device according to claim 7, wherein said opening is provided at said second tip end.

9. The prosthetic device according to claim 6, comprising a hip prosthesis and including an acetabular cup, wherein said acetabular cup has a wall delimited by said outer surface and by said inner surface, wherein said outer surface is convex and said inner surface is concave, wherein said wall accommodates in its thickness a plurality of cavities at said holes or ports.

10. The device according to claim 9, comprising a joint insert placed in contact with said inner surface of said acetabular cup and suitable for closing from the inside said plurality of cavities.

11. The prosthetic device according to claim 6, comprising a hip prosthesis and including a head component intended to be implanted in the acetabulum of a patient, and wherein the stem component delimited by said wall is intended to be implanted in the femur of a patient, said stem component protruding from said head component.

12. A kit for the implementation of a prosthetic device comprising or able to be added with an antibiotic or a medical substance, comprising a prosthetic device according to claim 1, and a filler material.

13. The kit according to claim 12, wherein said filler material is a fluid or a solid or a solidifiable fluid.

14. The kit according to claim 12, wherein said filler material comprises at least one among the following materials: acrylic resin, composite material comprising calcium phosphate or an inorganic salt, calcium sulphate, bioglass, polyvinyl alcohol, or an acrylic resin or PMMA and an inorganic salt or calcium phosphate or tri-calcium phosphate (TCP) or a thread of silk or cotton, or a biocompatible vegetable fibre or a woven or non-woven fabric, or a semi-solid biocompatible insoluble or soluble material, or wherein said semi-solid insoluble material is bone cement or wherein said semi-solid soluble material is animal collagen, sugars, cellulose, etc., or a mixture thereof.

15. The kit according to claim 12, wherein said filler material is suitable for absorbing or getting soaked in an antibiotic or medical substance or a solution comprising an antibiotic or medical substance and for releasing it to the outside of said prosthetic device by means of holes or ports present in said prosthetic body.

* * * * *